US009649016B2

(12) United States Patent
Wada et al.

(10) Patent No.: US 9,649,016 B2
(45) Date of Patent: May 16, 2017

(54) ENDOSCOPIC CAMERA AND ENDOSCOPIC DEVICE

(75) Inventors: Jyouji Wada, Kanagawa (JP); Yuuichi Takenaga, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 79 days.

(21) Appl. No.: 14/003,071

(22) PCT Filed: Feb. 29, 2012

(86) PCT No.: PCT/JP2012/001380
§ 371 (c)(1),
(2), (4) Date: Sep. 4, 2013

(87) PCT Pub. No.: WO2012/120837
PCT Pub. Date: Sep. 13, 2012

(65) Prior Publication Data
US 2014/0012080 A1 Jan. 9, 2014

(30) Foreign Application Priority Data
Mar. 10, 2011 (JP) .................................. 2011-052571

(51) Int. Cl.
A61B 1/06 (2006.01)
A61B 1/00 (2006.01)
A61B 1/05 (2006.01)
A61B 1/04 (2006.01)

(52) U.S. Cl.
CPC ...... *A61B 1/00174* (2013.01); *A61B 1/00183* (2013.01); *A61B 1/04* (2013.01); *A61B 1/05* (2013.01)

(58) Field of Classification Search
USPC ................ 600/127, 129, 133, 157, 169, 173
See application file for complete search history.

(56) References Cited

U.S. PATENT DOCUMENTS 3,145,249 A * 8/1964 Meltzer .......................... 359/508
3,856,000 A * 12/1974 Chikama ........................ 600/173
3,896,793 A * 7/1975 Mitsui et al. .................. 600/104
(Continued)

FOREIGN PATENT DOCUMENTS

JP 06-121567 4/1994
JP 07-327916 12/1995
(Continued)

OTHER PUBLICATIONS

Japanese Office Action having mail date of Sep. 30, 2014.
Search report from International Search Report in PCT/JP2012/001380, mail date is Jun. 12, 2012.

Primary Examiner — Matthew J Kasztejna
(74) Attorney, Agent, or Firm — Greenblum & Bernstein, P.L.C.

(57) ABSTRACT

Provided is an endoscopic camera capable of expanding its visual field up to an oblique back side. An endoscopic camera includes: a rigid case having a cylindrical shape with a top end portion being obliquely cut off; a camera head provided at the top end portion of the rigid case; a semispherical cover mounted on the top end portion of the rigid case to cover at least a part of the camera head; and a tilt motor adapted to rotate the camera head around a tilt shaft.

13 Claims, 6 Drawing Sheets

(56) References Cited

U.S. PATENT DOCUMENTS

| | | | |
|---|---|---|---|
| 5,575,754 A * | 11/1996 | Konomura | 600/117 |
| 5,762,603 A * | 6/1998 | Thompson | 600/112 |
| 6,277,064 B1 * | 8/2001 | Yoon | 600/114 |
| 6,309,345 B1 * | 10/2001 | Stelzer et al. | 600/106 |
| 6,364,830 B1 * | 4/2002 | Durell | 600/173 |
| 6,638,216 B1 * | 10/2003 | Durell | 600/173 |
| 6,648,817 B2 * | 11/2003 | Schara et al. | 600/173 |
| 6,916,286 B2 * | 7/2005 | Kazakevich | 600/173 |
| 7,066,879 B2 * | 6/2006 | Fowler et al. | 600/102 |
| 7,175,593 B2 * | 2/2007 | Durell | A61B 1/00165 600/130 |
| 7,344,494 B2 * | 3/2008 | Hoeg et al. | 600/173 |
| 7,347,860 B2 * | 3/2008 | Ouchi | 606/46 |
| 7,448,993 B2 * | 11/2008 | Yokoi et al. | 600/114 |
| 7,553,277 B2 * | 6/2009 | Hoefig et al. | 600/173 |
| 7,625,338 B2 * | 12/2009 | Gilad et al. | 600/173 |
| 7,662,094 B2 * | 2/2010 | Iddan | A61B 1/00096 348/340 |
| 8,075,478 B2 * | 12/2011 | Campos | 600/139 |
| 8,088,065 B2 * | 1/2012 | Karasawa et al. | 600/157 |
| 8,277,373 B2 * | 10/2012 | Maahs et al. | 600/107 |
| 8,376,932 B2 * | 2/2013 | Hashiba et al. | 600/104 |
| 8,485,968 B2 * | 7/2013 | Weimer et al. | 600/173 |
| 8,562,513 B2 * | 10/2013 | Yamatani | 600/106 |
| 8,702,597 B2 * | 4/2014 | Iddan | 600/167 |
| 8,870,758 B2 * | 10/2014 | Dahmen et al. | 600/173 |
| 2005/0096502 A1 * | 5/2005 | Khalili | 600/106 |
| 2005/0124858 A1 * | 6/2005 | Matsuzawa | A61B 1/00096 600/176 |
| 2006/0129032 A1 | 6/2006 | Durell | |
| 2006/0264709 A1 * | 11/2006 | Fujimori | A61B 1/00029 600/130 |
| 2007/0055103 A1 | 3/2007 | Hoefig et al. | |
| 2007/0055105 A1 * | 3/2007 | Matsuzawa | A61B 1/00096 600/176 |
| 2009/0048486 A1 * | 2/2009 | Surti | 600/127 |
| 2009/0062605 A1 | 3/2009 | Orihara et al. | |
| 2011/0211052 A1 | 9/2011 | Kogane | |
| 2013/0242071 A1 | 9/2013 | Wada et al. | |
| 2014/0249369 A1 * | 9/2014 | Hanabusa | A61B 1/00183 600/109 |

FOREIGN PATENT DOCUMENTS

| | | |
|---|---|---|
| JP | 11-337844 | 12/1999 |
| JP | 2004-156749 | 6/2004 |
| JP | 2007-75604 | 3/2007 |
| JP | 2007-509710 | 4/2007 |
| JP | 2009-56058 | 3/2009 |
| JP | 2009-125188 | 6/2009 |

* cited by examiner

FIG.6
(a)
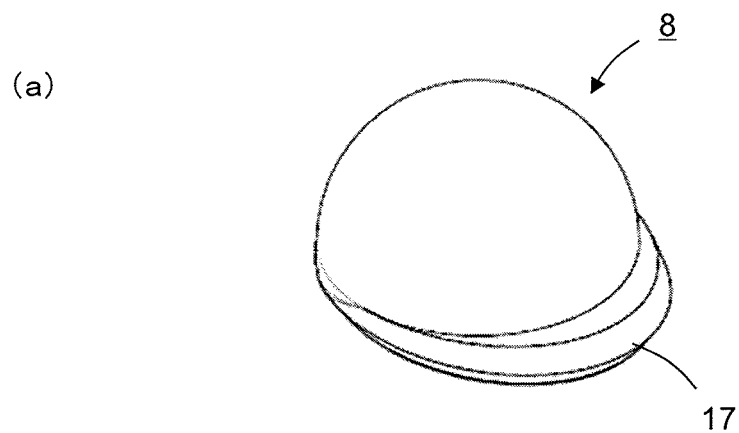
(b)
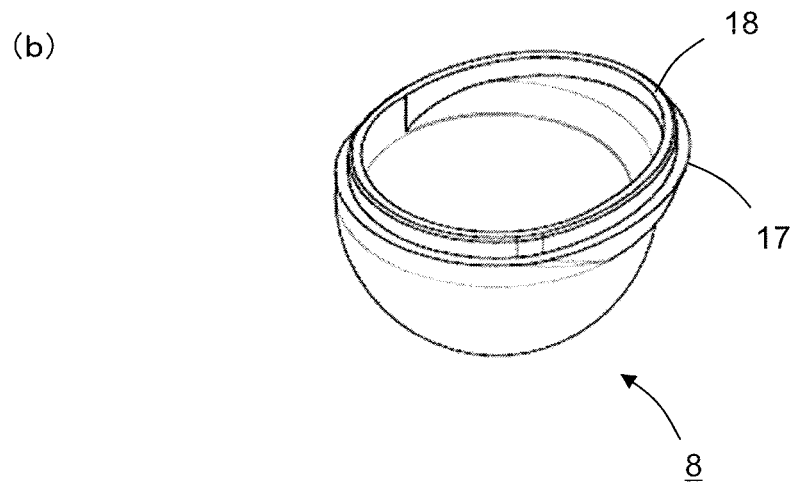

ENDOSCOPIC CAMERA AND ENDOSCOPIC DEVICE

TECHNICAL FIELD

The present invention relates to an endoscopic camera and an endoscopic device having an expanded visual field.

BACKGROUND ART

In various fields such as a medical field and an industrial field, a rigid endoscope camera has conventionally been used (see, for example, Patent Literatures 1 and 2). Such an endoscopic camera is required to have a function to change the direction of the visual field of the endoscopic camera in accordance with use applications or observation objects. Accordingly, a conventional endoscopic camera includes a mechanism for changing a photographing direction of an imaging unit (direction of the visual field of the endoscopic camera) in accordance with use applications or observation objects.

CITATION LIST

Patent Literature

Patent Literature 1: Japanese Patent Application Laid-Open No. 7-327916
Patent Literature 2: Japanese Patent Application Laid-Open No. 2009-125188

SUMMARY OF INVENTION

Technical Problem

However, while the conventional endoscopic camera can change the direction of the visual field by rotating the imaging unit in a tilt direction, the range of a changeable direction of the visual field is limited to the front side of a camera head. In short, in the conventional endoscopic camera, the back side of the camera head cannot be included in the visual field (the back side of the camera head cannot be photographed).

The present invention has been made to solve the aforementioned conventional problem, and an object of the present invention is to provide an endoscopic camera and an endoscopic device capable of expanding its visual field up to an oblique back side.

Solution to Problem

An endoscopic camera of the present invention is adapted to include: a rigid case having a cylindrical shape with a top end portion being obliquely cut off; a camera head provided at the top end portion of the rigid case while at least a part of the camera head is exposed to an outside from the top end portion of the rigid case; a semispherical cover mounted on the top end portion of the rigid case to cover an exposed part of the camera head with a specified clearance present between the semispherical cover and the camera head; and a rotation driving unit adapted to rotate the camera head around a specified rotating axis, wherein the rotating axis is provided so as to pass through a center of the camera head and to position on a plane formed by obliquely cutting off the top end portion of the rigid case.

With this configuration, a semispherical cover is obliquely mounted on the top end portion of the rigid case, and a camera head is rotated inside the semispherical cover which is obliquely mounted thereon. In this case, the rotating axis (tilt axis) of the camera head is provided so as to pass through the center of the camera head and to be vertical to a central axis of the rigid case on the plane obtained by obliquely cutting off the top end portion of the rigid case. Therefore, by rotating the camera head, the back side (oblique back side) of the camera head can be photographed.

Further, in the endoscopic camera of the present invention, the endoscopic camera is adapted to include a plate-like belt which has a thickness smaller than the clearance and which has both end portions being fixed to the camera head so that the camera head is retained while being sandwiched from both sides, and the rotation driving unit is provided inside the rigid case at a position different from that of the camera head and is adapted to rotate the camera head around the rotating shaft by pulling one end portion of the belt.

With this configuration, at the top end portion of the cylindrical rigid case, the camera head is retained while being sandwiched from both sides with the plate-like belt. Since the camera head can be positioned with the plate-like belt in this way, it is not necessary to provide another mechanism that positions the camera head on the periphery of the camera head at the top end portion of the rigid case. Moreover, when the camera head is rotated around the rotating axis (tilt axis), rotation driving force (force to pull and push the belt) is transmitted from the rotation driving unit to the camera head through the plate-like belt. In this case, the rotation driving unit is placed inside the rigid case at a position different from that of the camera head. Accordingly, it is not necessary to provide another mechanism that rotates the camera head on the periphery of the camera head at the top end portion of the rigid case. Therefore, since one configuration that is a plate-like belt can implement both a function to retain the camera head and a function to rotate the camera head, downsizing (downsizing which is difficult with a retention mechanism and a rotation mechanism being separately provided) of the endoscopic camera is achieved.

Further, the endoscopic camera of the present invention is adapted so that a flange portion is extendedly provided from an edge of the semispherical cover toward an outside, and a joint portion to be joined with the rigid case is provided at a top end portion of the flange portion.

With this configuration, it becomes possible to expand an inner space of the rigid case and to thereby facilitate insertion of a large-diameter camera head 7 into the rigid case.

An endoscopic device of the present invention is adapted to include an above-described endoscopic camera and a signal processing unit adapted to perform specified signal processing on a video signal acquired from the endoscopic camera.

The endoscopic device can also photograph the back side (oblique back side) of the camera head by rotating the camera head inside the obliquely mounted semispherical cover as in the case of the above-described endoscopic camera.

Advantageous Effects of Invention

The present invention can provide an endoscopic camera having an effect of being able to expand its visual field up to an oblique back side.

BRIEF DESCRIPTION OF DRAWINGS

FIGS. 6a and 6b are perspective views of a semispherical cover (modified example) in the embodiment of the present invention.

DESCRIPTION OF EMBODIMENT

Figure 1:
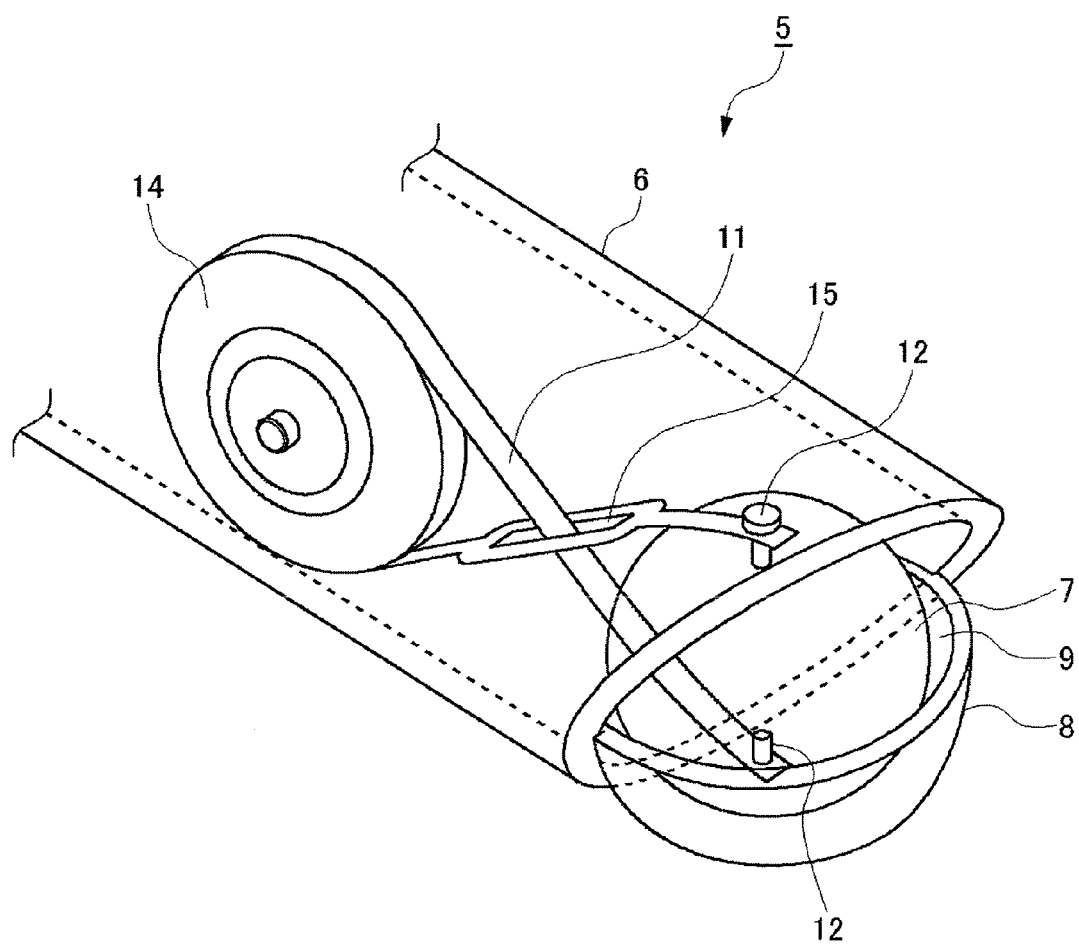
FIG. 1 is an explanatory view showing a principal part of an endoscopic camera in an embodiment of the present invention.

Hereinafter, an endoscopic device in an embodiment of the present invention will be described with reference to the drawings. In the present embodiment, there is shown a case of an endoscopic device used as an abdominoscope and the like that observe an abdominal cavity.

The configuration of the endoscopic device in the embodiment of the present invention will be described with reference to FIGS. 1 to 4. First, with reference to FIG. 2, the configuration of the entire endoscopic device will be described. As shown in FIG. 2, an endoscopic device 1 includes a main body unit 4 that incorporates a signal processing unit 2, a light source unit 3 and the like, and an endoscopic camera 5 removably mounted on the main body unit 4. The signal processing unit 2 has a function to perform specified signal processing on a video input signal acquired from the endoscopic camera 5 to generate a video output signal that is to be outputted to a monitor (not shown) and the like. The light source unit 3 has a function to send illumination light to the endoscopic camera 5 with use of an optical fiber (not shown) and the like.

Figure 2:
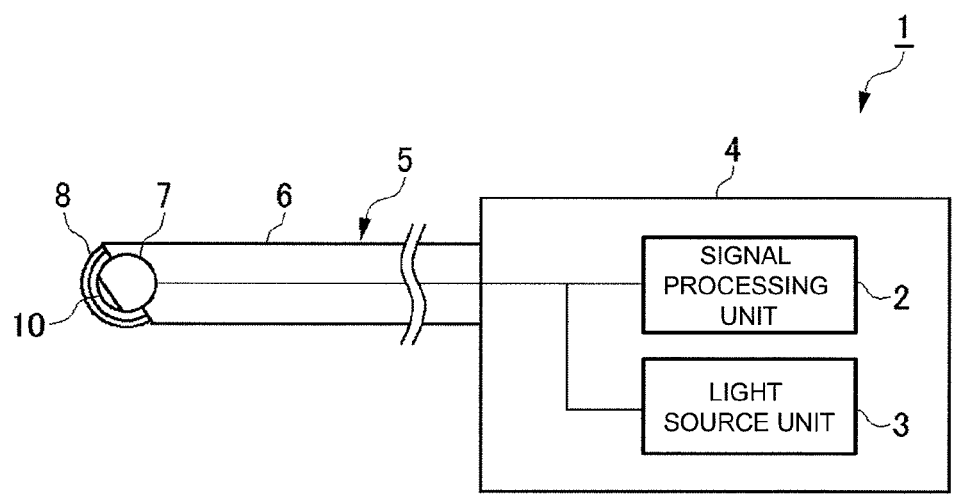
FIG. 2 is a block diagram of an endoscopic device in the embodiment of the present invention.
Figure 3:
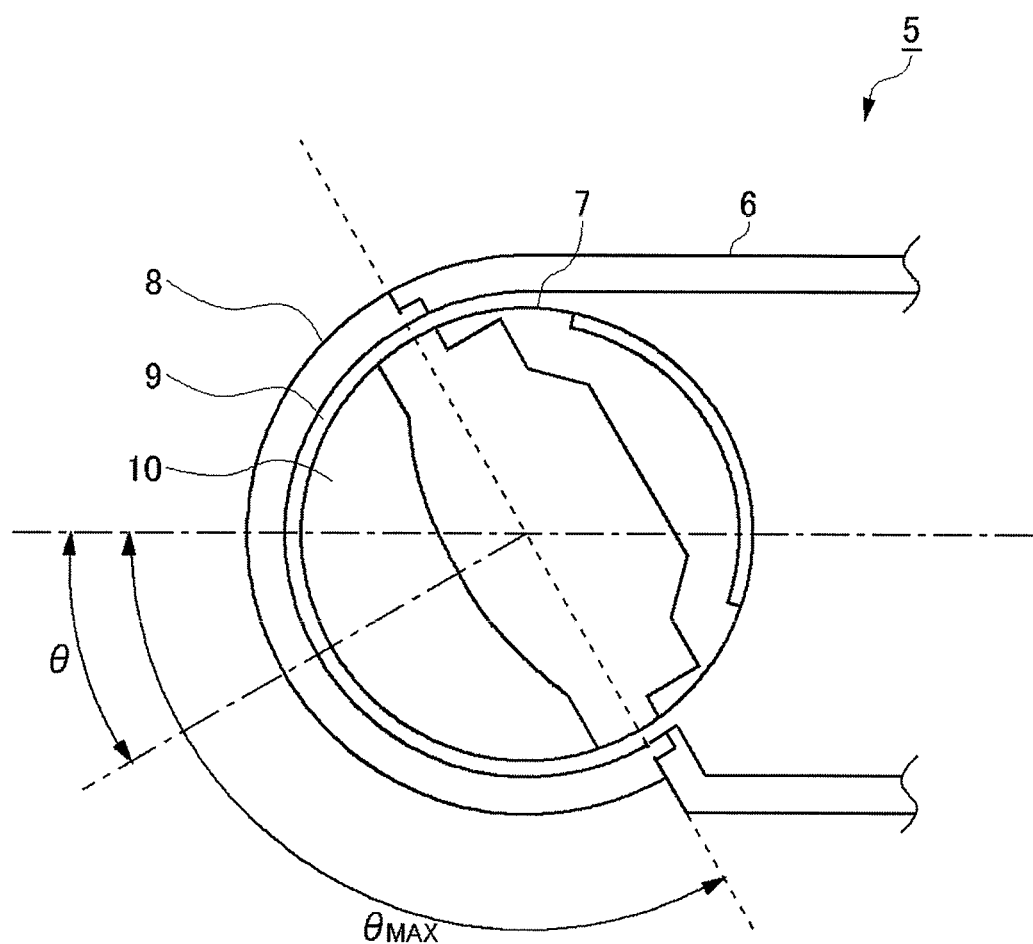
FIG. 3 is an enlarged view showing a principal part of an endoscopic camera in the embodiment of the present invention.
Figure 4:
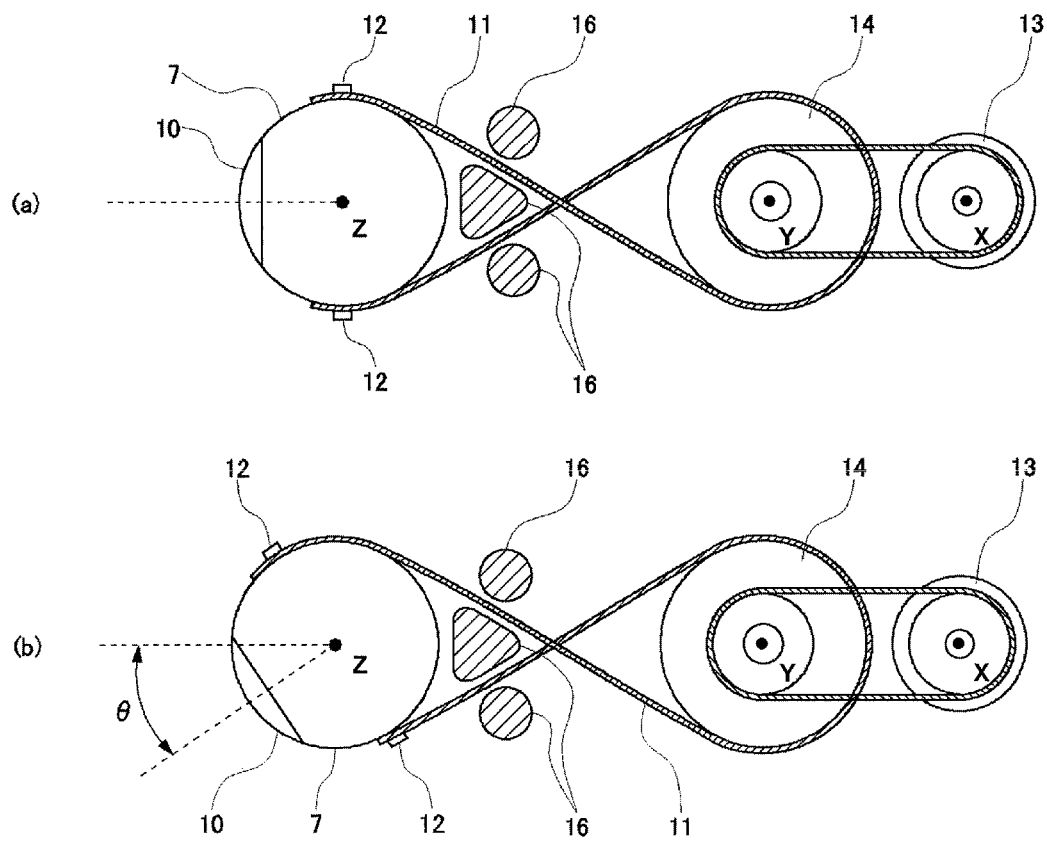
FIGS. 4a and 4b are explanatory views of a rotation mechanism in a tilt direction in the embodiment of the present invention.

A description is now given of the configuration of the endoscopic camera 5 with reference to FIGS. 1, 3, and 4. As shown in FIG. 1, the endoscopic camera 5 includes a rigid case 6 having a cylindrical shape with a top end portion being obliquely cut off, and a spherical camera head 7 provided at the top end portion of the rigid case 6. In this example, a part (generally half) of the camera head 7 is exposed to an outside from the top end portion of the rigid case 6, and a remainder (a remaining half) of the camera head 7 is housed in the rigid case 6. The top end portion of the rigid case 6 has a semispherical cover 8 provided to cover the exposed portion of the camera head 7. The cover 8 is made from a transparent optical glass or an optical plastic. Note that a specified clearance 9 is provided between the camera head 7 and the cover 8. Note that although only a part of the cover 8 is shown in FIG. 1 for the sake of explanation, the cover 8 has a ½ sphere (semi-sphere) shape in actuality.

As shown in FIG. 3, the camera head 7 includes a lens 10. As shown in FIG. 1, both ends of a tilt belt 11 are respectively fixed at positions of a pair of upper and lower poles which are shifted from an optical axis of the lens 10 by 90 degrees on the spherical surface of the camera head 7. In this case, the tilt belt 11 has a thickness smaller than the clearance 9 between the camera head 7 and the cover 8. The tilt belt 11 is fixed to the camera head 7 with use of fixing bolts 12.

Rotation driving force of a tilt motor 13 is transmitted to the tilt belt 11 through a pulley 14. As shown in FIG. 4, when one end portion of the tilt belt 11 is pulled while the other end portion of the tilt belt 11 is pushed out by the rotation driving force of the tilt motor 13, the camera head 7 is rotated around a tilt axis in a tilt direction. The tilt motor 13 corresponds to a rotation driving unit of the present invention. Note that a vertical direction of an image taken with the endoscopic camera 5 and displayed on a monitor corresponds to the "tilt direction". The tilt axis is provided so as to pass through the center of the sphere of the camera head 7 and to position on a plane obtained by obliquely cutting off the top end portion of the rigid case 6. The tilt axis is vertical to the central axis of the rigid case 6.

In the present embodiment, the tilt motor 13 and the pulley 14 are provided inside the rigid case 6 at positions different from that of the camera head 7 (rear positions inside the rigid case 6). In other words, a rotating shaft (a rotating shaft X of the tilt motor 13, or a rotating shaft Y of the pulley 14) that generates rotation driving force to drive the camera head 7 in the tilt direction is placed at a position different from the position of a rotating axis (tilt axis Z) of the camera head 7 (see FIG. 4).

Further, as shown in FIGS. 1 and 4, the tilt belt 11 is crossed between the camera head 7 and the pulley 14, and a belt insertion hole 15 is provided in a position where the tilt belt 11 is crossed. Note that as shown in FIG. 4, a guide unit 16 that guides the tilt belt 11 may be provided inside the rigid case 6 in the case where the tilt belt 11 is crossed.

Figure 5:
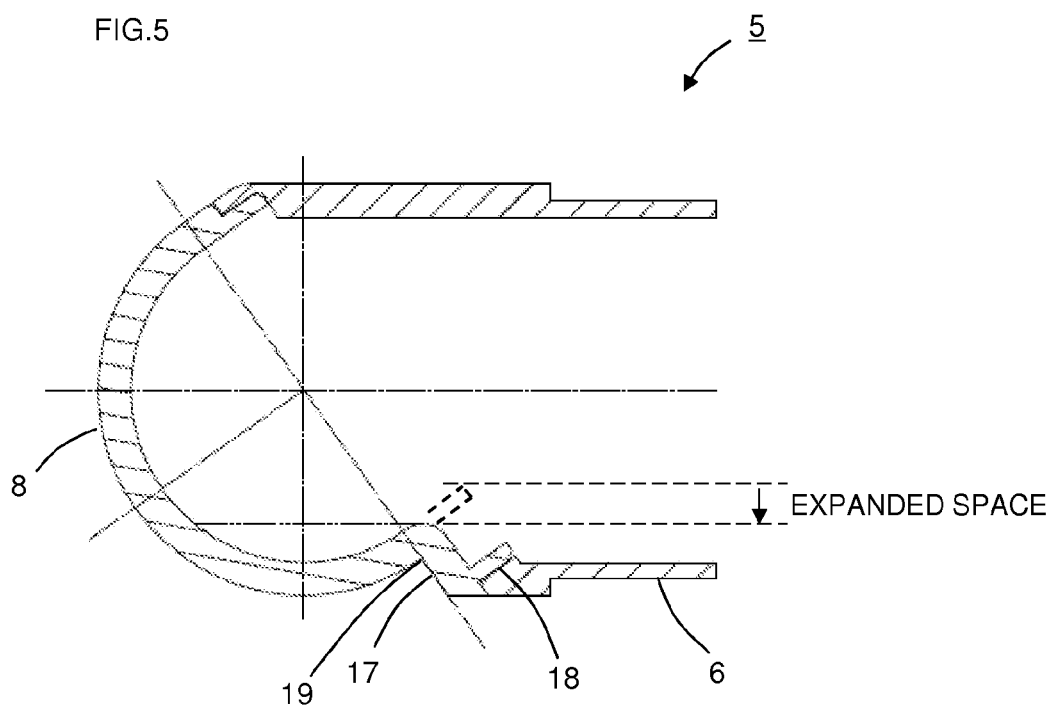
FIG. 5 is an explanatory view of a mounting configuration of a semispherical cover (modified example) in the embodiment of the present invention.

Moreover, as shown in FIGS. 5 and 6, a flange portion 17 may be provided at an edge of the semispherical cover 8. For example, a half-elliptical flange portion 17 may extendedly be provided so as to spread from a semicircular part on the lower side (lower side in FIG. 5) of the edge (circular edge) of the semispherical cover 8 toward the outside (from the center of the semispherical cover 8 toward the outside), and a joint portion 18 to be joined with the rigid case 6 is provided at the top end portion of the flange portion 17. Note that the lower side (lower side in FIG. 5) of the cover 8 refers to the side to which a zenith direction of the semispherical cover 8 is tilted (the side to which a tilt angle is expanded) when the cover 8 is obliquely mounted on the top end portion of the rigid case 6 (see FIG. 3). In addition, a recess portion 19 is defined between the semispherical cover 8 and the case 6. As shown in FIG. 5, the recess portion 19 is defined between the edge of the semispherical cover 8 and the flange portion 17.

According to such an endoscopic camera 5 of the present embodiment, the visual field can be expanded up to the oblique back side. More specifically, in the present embodiment, the semispherical cover 8 is obliquely mounted on the top end portion of the rigid case 6, and the spherical camera head 7 is rotated inside the semispherical cover 8 which is obliquely mounted thereon. In this case, the rotating shaft (tilt shaft) of the camera head 7 is provided so as to pass through the center of the camera head 7 and to be vertical to the central axis of the rigid case 6 on the plane obtained by obliquely cutting off the top end portion of the rigid case 6. Therefore, by rotating the camera head 7, the back side (oblique back side) of the camera head 7 can be photographed.

For example, in the case where the rigid case 6 has a cylindrical shape with the top end portion being obliquely cut off at an angle $\theta_{MAX}$ ($\theta_{MAX}>90°$) as shown in FIG. 3, a tilt angle $\theta$ of the camera head 7 can take a value in an angle range of 0° to $\theta_{MAX}$. Thus, in the present embodiment, the visual field is expanded to the oblique back side of the camera head 7. Note that in this case, tilt angle $\theta=0°$ corresponds to the direction of the central axis of the rigid case 6. Further, it is possible to set the angle $\theta_{MAX}$ at an arbitrary angle (provided that the angle is larger than 90°) depending on application of the endoscopic camera 5 or the like.

Moreover, according to the present embodiment, at the top end portion of the cylindrical rigid case 6, the spherical camera head 7 is retained while being sandwiched from both sides with the plate-like belt. Since the position of the camera head 7 can be set with the plate-like belt in this way, it is not necessary to provide another mechanism that positions the camera head 7 on the periphery of the camera head 7 at the top end portion of the rigid case 6. Moreover, when the camera head 7 is rotated around the rotating axis (tilt axis), rotation driving force (force to pull and push the belt) is transmitted from the rotation driving unit to the camera head 7 through the plate-like belt.

In this case, the rotation driving unit is placed inside the rigid case 6 at a position different from that of the camera head 7. Accordingly, it is not necessary to provide another mechanism that rotates the camera head on the periphery of the camera head at the top end portion of the rigid case 6. Therefore, since one configuration that is a plate-like belt can implement both the function to retain the camera head 7 and the function to rotate the camera head 7, downsizing (downsizing which is difficult with a retention mechanism and a rotation mechanism being separately provided) of the endoscopic camera 5 is achieved.

In the present embodiment, the cover 8 is obliquely mounted on the top end portion of the rigid case 6. Accordingly, if the joint portion 18 is provided on the lower edge of the semispherical cover 8 as it is (shown with a broken line in FIG. 5), an inner space of the rigid case 6 is diminished by the joint portion 18, which makes it difficult to insert the large-diameter camera head 7 into the rigid case 6. In this case, the flange portion 17 is extendedly provided from the lower edge of the semispherical cover 8 toward the outside, and the joint portion 18 to be joined with the rigid case 6 is provided at the top end portion of the flange portion 17. As a result, the inner space of the rigid case 6 can be expanded, which makes it easy to insert the large-diameter camera head 7 into the rigid case 6.

Although the embodiment of the present invention has been described in an illustrative manner, it should be understood that the scope of the present invention is not limited to the embodiment disclosed, and modifications and variations depending on purposes are possible within the scope stated in the claims.

For example, in the above embodiment, the entire camera head 7 has been described as a sphere. However, the scope of the present invention is not limited thereto, and at least a portion of the camera head 7 that faces the cover 8 at the time of rotation may be a spherical shape.

INDUSTRIAL APPLICABILITY

As described in the foregoing, the endoscopic device according to the present invention has the effect of being able to expand the visual field up to the oblique back side and therefore is useful as a device such as an endoscopic camera for medical use and industrial use.

REFERENCE SIGNS LIST

1 Endoscopic device
2 Signal processing unit
3 Light source unit
4 Main body unit
5 Endoscopic camera
6 Rigid case
7 Camera head
8 Cover
9 Clearance
10 Lens
11 Tilt belt
12 Bolt
13 Tilt motor (rotation driving unit)
14 Pulley
15 Belt insertion hole
16 Guide unit
17 Flange portion
18 Joint portion
19 Recess portion

What is claimed is:

1. An endoscopic camera, comprising:
a cylindrical case having a distal end configured such that a top end portion of the cylindrical case extends further outward than a bottom end portion thereof in an axial direction of the cylindrical case;
a camera head provided at the distal end of the cylindrical case, a part of which is exposed to an outside of the cylindrical case from the distal end of the cylindrical case;
a cover which is mounted on the distal end of the cylindrical case to cover the part of the camera head; and
a rotation driver adapted to rotate the camera head around a specified rotating axis, wherein
the cover has a flange portion exposed to the outside of the cylindrical case,
the flange portion projects from an edge of the cover and extends downwardly at an inclined angle in a direction away from the camera head, and
a lower side portion of the flange portion facing the cylindrical case is connected to an edge of the cylindrical case.

2. The endoscopic camera according to claim 1, wherein the lower side portion of the flange portion includes a joint portion that protrudes toward and connects to the edge of the cylindrical case.

3. The endoscopic camera according to claim 1, wherein the rotating axis is provided so as to pass through a center of the camera head and positioned on a plane extending between the top end portion and the bottom end portion of the cylindrical case.

4. The endoscopic camera according to claim 3, wherein the top end portion of the cylindrical case has a curved surface portion that is connectable to the cover.

5. The endoscopic camera according to claim 3, further comprising:
a recess portion defined between a curved surface of the cover and the flange portion.

6. The endoscopic camera according to claim 1, wherein the top end portion of the cylindrical case has a curved surface portion that is connectable to the cover.

7. The endoscopic camera according to claim 1, further comprising:
a recess portion defined between a curved surface of the cover and the flange portion.

8. The endoscopic camera according to claim 1, wherein the endoscopic camera includes a plate-like belt which has a thickness smaller than a clearance between the cover and the camera head and which has two end portions being fixed to the camera head so that the camera head is retained while being sandwiched between the two end portions, and the rotation driver is provided inside the cylindrical case and is adapted to rotate the camera head around the rotating axis when one end portion of the belt is pulled.

9. The endoscopic camera according to claim 1, wherein the flange portion has an inclined surface being in a plane including the rotating axis.

10. The endoscopic camera according to claim 1, wherein the flange portion has an inclined surface,
an angle between a central axis of the cylindrical case and an extended line from the inclined surface is greater than 90 degrees.

11. The endoscopic camera according to claim 10, wherein
the rotation driver is configured to rotate the camera head in a tilt direction within at least the angle between the central axis of the cylindrical case and the extended line from the inclined surface.

12. The endoscopic camera according to claim 11, wherein
when the camera head is rotated in the tilt direction, the endoscopic camera is configured to capture an image of an object disposed behind a recess portion of the endoscopic camera defined by a curved surface of the cover and the flange portion.

13. An endoscopic device, comprising:
an endoscopic camera according to claim 1; and
a signal processor adapted to perform specified signal processing on a video signal acquired from the endoscopic camera.

* * * * *